United States Patent
Lyons

(10) Patent No.: US 6,872,705 B2
(45) Date of Patent: Mar. 29, 2005

(54) USE OF ANTIMICROBIAL PEPTIDES AS PRESERVATIVES IN OPHTHALMIC PREPARATIONS, INCLUDING SOLUTIONS, EMULSIONS, AND SUSPENSIONS

(75) Inventor: Robert T. Lyons, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 272 days.

(21) Appl. No.: 09/904,753

(22) Filed: Jul. 13, 2001

(65) Prior Publication Data

US 2003/0092612 A1 May 15, 2003

(51) Int. Cl.[7] .......................... A61K 38/04; A61K 38/16
(52) U.S. Cl. .......................... 514/13; 514/14; 514/912; 530/326; 600/563
(58) Field of Search .......................... 514/13, 14, 912; 530/326; 600/563

(56) References Cited

U.S. PATENT DOCUMENTS

| 4,525,346 A |   | 6/1985  | Stark ........................... 424/80 |
| 5,171,526 A |   | 12/1992 | Wong et al. .................. 422/28 |
| 5,200,453 A |   | 4/1993  | Janssen ....................... 514/399 |
| 5,474,979 A | * | 12/1995 | Ding et al. ................... 514/11 |
| 5,549,894 A | * | 8/1996  | Hunt ........................ 424/94.64 |
| 5,736,165 A | * | 4/1998  | Ripley et al. ............... 424/661 |
| 5,792,831 A | * | 8/1998  | Maloy ......................... 530/326 |
| 5,830,508 A |   | 11/1998 | MacKeen .................... 424/602 |
| 5,993,864 A | * | 11/1999 | Kross ......................... 424/661 |
| 6,372,234 B1 | * | 4/2002  | Deckers et al. ............. 424/401 |
| 6,482,799 B1 | * | 11/2002 | Tuse et al. ................... 514/14 |

FOREIGN PATENT DOCUMENTS

WO      WO 96/25183        8/1996

OTHER PUBLICATIONS

Darveau et al., "Beta–Lactam Antibiotics Potentiate Magainin 2 Antimicrobal Activity In Vitro and In Vivo," Antimicrobial Agents and Chemotherapy, Jun. 1991, p. 1153–1159.*

Matsuzaki et al., "Mechanism of Synergism between Antimicrobial Peptides Magainin 2 and PGLa," Biochemistry, 1998, 37, 15144–15153.*

Maria Bishop, "DG Dispatch–ACR: Topical Cyclosporin A Restores Clear Vision to Sjogren's Syndrome Patients", Doctor's Guide Global Edition, www.pslgroup.com/dg/le96aa.htm, Nov. 3, 2000.

J.H. Lee et al., "High–Level Expression of Antimicrobial Peptide Mediated by a Fusion Partner Reinforcing Formation of Inclusion Bodies", Biochemical and Biophysical Research Communications 277, 575–580, (2000).

Stevenson, D., MD et al., "Cyclosporin A Ophthalmic Emulsion in the Treatment of Moderate to Severe Dry Eye Disease", Eye News Late 2000–Richmond Eye Associates from Ophthalmology May 2000; 107:967–974.

Gao J, et al., Abstract of "The role of apoptosis in the pathogenesis of canine keratoconjunctivitis sicca: the effect of topical Cyclosporin A therapy", Department of Biological Science, Allergan, Inc. Cornea Nov. 1998; 17(6): 654–63.

Andrew Acheampong et al., "Distribution of cyclosporin A in ocular tissues after topical administration to albino rabbits and beagle dogs", Current Eye Research 1999, vol. 18, No. 2, pp. 91–103.

Sall K, et al., Abstract of "Two multicenter, randomized studies of the efficacy and safety of cyclosporine ophthalmic emulsion in moderate to severe dry eye disease. ScA Phase 3 Study Group.", Ophthalmology Apr. 2000;107(4): 631–9.

Stevenson D., Abstract of "Efficacy and safety of cyclosporin A ophthalmic emulsion in the treatment of moderate–to–severe dry eye disease: a dose–ranging, randomized trial. The Cyclosporin A Phase 2 Study Group.", Ophthalmology May 2000; 107(5):967–74.

Katsumi Matsuzaki, "Why and how are peptide–lipide interactions utilized for self–defence? Magainins and tachyplesins as archetypes", Biochimica et Biophysica Acta 1462 (1999) 1–10.

David Andreu, "Animal Antimicrobial Peptides: An Overview", Biopolymers (Peptide Science), vol. 47, 415–433 (1998).

Katsumi Matsuaki, "Magainins as paradign for the mode of action of pore forming polypeptides", Biochimica et Biophysica Acta 1376 (1998) 391–400.

W. Lee Malloy et al., "Structure–Activity Studies on Magainins and Other Host Defense Peptides", Biopolymers (Peptide Science), vol. 37, 105–122 (1995).

Michael Zasloff et al., "Antimicrobial activity of synthetic magainin peptides and several analogues", Proc. Natl. Acad. Sci. USA, vol. 85, pp. 910–913, Feb. 1988, Microbiology.

* cited by examiner

*Primary Examiner*—Robert A. Wax
(74) *Attorney, Agent, or Firm*—Stout, Uxa, Buyan & Mullins, LLP; Frank J. Uxa; Greg S. Hollrigel

(57) ABSTRACT

Methods for preserving ophthalmic compositions are disclosed. In one embodiment, such compositions include a liquid medium and an antimicrobial component which is preferably substantially non-oxidative. Compositions which include a liquid medium and antimicrobial peptide magainins, present in an amount effective as a preservative, are also disclosed. Preserved compositions useful for administering a therapeutic component to the eyes or caring for contact lenses are also included within the scope of the present invention.

22 Claims, No Drawings

SEQUENCE LISTING

<160> NUMBER OF SEQ ID NOS: 14

<210> SEQ ID NO 1
<211> LENGTH: 23
<212> TYPE: PRT
<213> ORGANISM: Xenopus laevis
<300> PUBLICATION INFORMATION:
<301> AUTHORS: Lee et al.,
<302> TITLE: High-Level Expression of Antimicrobal Peptide Mediated
      by a Fusion Partner Reinforcing Formation of Inclusion
      Bodies
<303> JOURNAL: Biochem. Biophys. Res. Commun.
<304> VOLUME: 277
<306> PAGES: 575-580
<307> DATE: Sept 21, 2000

<400> SEQUENCE: 1

Gly Ile Gly Lys Phe Leu His Ser Ala Gly Lys Phe Gly Lys Ala Phe
 1               5                  10                  15

Val Gly Glu Ile Met Lys Ser
            20

<210> SEQ ID NO 2
<211> LENGTH: 23
<212> TYPE: PRT
<213> ORGANISM: Xenopus laevis

<400> SEQUENCE: 2

Gly Ile Gly Lys Phe Leu His Ser Ala Lys Lys Phe Gly Lys Ala Phe
 1               5                  10                  15

Val Gly Glu Ile Met Asn Ser
            20

<210> SEQ ID NO 3
<211> LENGTH: 22
<212> TYPE: PRT
<213> ORGANISM: Artificial Sequence
<220> FEATURE:
<221> NAME/KEY: PEPTIDE
<222> LOCATION: (22)
<223> OTHER INFORMATION: Xaa at position 22 is Lys-amide
<223> OTHER INFORMATION: Description of Artificial Sequence: maginin
      analog

<400> SEQUENCE: 3

Gly Ile Gly Lys Phe Leu Lys Lys Ala Lys Lys Phe Gly Lys Ala Phe
 1               5                  10                  15

Val Lys Ile Leu Lys Xaa
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: maginin
      analog

<400> SEQUENCE: 4

Gly Ile Gly Lys Phe Leu Lys Lys Ala Lys Lys Phe Gly Lys Ala Phe
 1               5                  10                  15

Val Lys Ile Leu Lys Lys
            20

```
<210> SEQ ID NO 5
<211> LENGTH: 37
<212> TYPE: PRT
<213> ORGANISM: silk moth

<400> SEQUENCE: 5

Lys Trp Lys Leu Phe Lys Lys Ile Glu Lys Val Gly Gln Asn Ile Arg
 1               5                  10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 6
<211> LENGTH: 36
<212> TYPE: PRT
<213> ORGANISM: silk moth

<400> SEQUENCE: 6

Lys Trp Lys Val Phe Lys Lys Ile Glu Lys Met Gly Arg Asn Ile Arg
 1               5                  10                  15

Asn Gly Ile Val Lys Ala Gly Pro Ala Ile Ala Val Leu Gly Glu Ala
            20                  25                  30

Lys Ala Leu Gly
        35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: analog of
      cecropin B

<400> SEQUENCE: 7

Met Pro Arg Trp Arg Leu Phe Arg Arg Ile Asp Arg Val Gly Lys Gln
 1               5                  10                  15

Ile Lys Gln Gly Ile Leu Arg Ala Gly Pro Ala Ile Ala Leu Val Gly
            20                  25                  30

Asp Ala Arg Ala Val Gly
        35

<210> SEQ ID NO 8
<211> LENGTH: 30
<212> TYPE: PRT
<213> ORGANISM: human

<400> SEQUENCE: 8

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30

<210> SEQ ID NO 9
<211> LENGTH: 29
<212> TYPE: PRT
<213> ORGANISM: human

<400> SEQUENCE: 9

Cys Tyr Cys Arg Ile Pro Ala Cys Ile Ala Gly Glu Arg Arg Tyr Gly
 1               5                  10                  15

Thr Cys Ile Tyr Gln Gly Arg Leu Trp Ala Phe Cys Cys
```

```
                        20              25

<210> SEQ ID NO 10
<211> LENGTH: 30
<212> TYPE: PRT
<213> ORGANISM: human

<400> SEQUENCE: 10

Asp Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30

<210> SEQ ID NO 11
<211> LENGTH: 33
<212> TYPE: PRT
<213> ORGANISM: rabbit

<400> SEQUENCE: 11

Val Val Cys Ala Cys Arg Arg Ala Leu Cys Leu Pro Arg Glu Arg Arg
 1               5                  10                  15

Ala Gly Phe Cys Arg Ile Arg Gly Arg Ile His Pro Leu Cys Cys Arg
            20                  25                  30

Arg

<210> SEQ ID NO 12
<211> LENGTH: 11
<212> TYPE: PRT
<213> ORGANISM: cow

<400> SEQUENCE: 12

Arg Leu Cys Arg Val Val Ile Arg Val Cys Arg
 1               5                  10

<210> SEQ ID NO 13
<211> LENGTH: 26
<212> TYPE: PRT
<213> ORGANISM: Artificial Sequence
<220> FEATURE:
<221> NAME/KEY: PEPTIDE
<222> LOCATION: (26)
<223> OTHER INFORMATION: Xaa at position 26  is Ser-amide
<223> OTHER INFORMATION: Description of Artificial Sequence: Hybrid
      antimicrobial peptide

<400> SEQUENCE: 13

Lys Trp Lys Leu Phe Lys Lys Ile Gly Ile Gly Ala Val Leu Lys Val
 1               5                  10                  15

Leu Thr Thr Gly Leu Pro Ala Leu Ile Xaa
            20                  25

<210> SEQ ID NO 14
<211> LENGTH: 16
<212> TYPE: PRT
<213> ORGANISM: Artificial Sequence
<220> FEATURE:
<221> NAME/KEY: PEPTIDE
<222> LOCATION: (16)
<223> OTHER INFORMATION: Xaa at position 16 is Leu-amide
<223> OTHER INFORMATION: Description of Artificial Sequence: Hybrid
      antimicrobial peptide
```

```
-continued

<400> SEQUENCE: 14

Lys Trp Lys Gly Ile Gly Ala Val Leu Lys Val Leu Thr Thr Gly Xaa
 1               5                  10                  15
```

USE OF ANTIMICROBIAL PEPTIDES AS PRESERVATIVES IN OPHTHALMIC PREPARATIONS, INCLUDING SOLUTIONS, EMULSIONS, AND SUSPENSIONS

BACKGROUND OF THE INVENTION

This invention relates to preserved ophthalmic compositions. More particularly, the present invention relates to preserved ophthalmic compositions, for example, useful in administering a therapeutic component to the eyes, and for example, to care for contact lenses, which include one or more peptides and/or peptide derivatives as antimicrobial agents.

Various compositions, such as solutions, emulsions and suspensions are used in association with administering therapeutic components to the eyes. For example, an oil-in-water emulsion may be used as a carrier for a therapeutic component to be administered to the eyes.

At present, no safe effective preservative exists for an oil-in-water emulsion product. This is because the most acceptable preservative, benzalkonium chloride, loses its effectiveness due to partitioning into the oil phase. As a result only single dose containers of oil-in-water emulsion ophthalmic compositions can be marketed up to this time.

Use of single dose containers to store ophthalmic compositions prevents contamination and growth of microorganisms. However, single dose containers are inconvenient to use and are expensive for the consumer. Appropriate use of an effective preservative will allow for production of multidose containers of preserved ophthalmic compositions such as oil-in-water emulsions.

Various compositions are used in association with contact lenses to ensure that the lenses may be safely, comfortably and conveniently worn. Contact lens care compositions, for example, cleaning compositions, wetting compositions, conditioning compositions and the like, often utilize at least one preservative, depending on the type of composition, for preserving the lens care composition itself.

A preserved contact lens care composition has sufficient antimicrobial activity so that when the composition is contacted with a contact lens substantially no increase in the microorganism population on the lens or in the composition is obtained. A preserved contact lens care composition may be termed a microbiostatic composition. Contact lens care compositions are often preserved to prevent any substantial increase in, or to gradually decrease, the population of contaminating microorganisms in the compositions and, thereby, to extend their shelf life.

Various compounds are known for use as preserving agents in preserved ophthalmic compositions. Examples include thimerosal, benzalkonium chloride and chlorhexidine. However, these preserving agents are known to exhibit ocular toxicity which may result in irritation or sensitivity to the eye. Further, a soft contact lens, a rigid gas permeable contact lens (RGP) or a hard contact lens can absorb or adsorb these compounds. This causes the contact lens to retain the irritating compound and contributes to the eye irritation and eye sensitivity which may result.

Thus, it is readily apparent that a continuing need exists for safe and efficacious compositions that can be used to preserve ophthalmic compositions.

SUMMARY OF THE INVENTION

New preserved compositions and methods employing such compositions, particularly compositions and methods directed to eye care and contact lens care, have been discovered. The present compositions include effective preservatives to protect against growth of contaminating microorganisms. Importantly, such preserving activities are achieved using the present compositions with little or no risk of eye irritation or sensitivity.

In one embodiment of the invention, compositions useful for preserving ophthalmic compositions are provided. Such compositions include a magainin antimicrobial peptide, an analog of a magainin antimicrobial peptide or a mixture thereof present in an amount effective as a preservative. This effective amount may be less than about 10 milligrams per milliliter or less than about 1 milligram per milliliter or less than about 0.1 milligram per milliliter. Also included in the compositions is a therapeutic component. In a particularly useful embodiment of the invention, the compositions comprise magainin antimicrobial peptides. In another particularly useful embodiment of the invention, the compositions comprise an analog of a magainin antimicrobial peptide comprising the amino acid sequence GIGKFLKKAKKF-GKAFVKILKK (SEQ ID NO: 4). The compositions may also include water and an effective amount of a buffer to provide the compositions with a desired pH. Also, the compositions may include an effective amount of a tonicity component to provide the compositions with a desired osmolality.

The compositions exist in various forms. For example, the compositions may be an oil-in-water emulsion, a solution or a suspension. Also, provided is for a sole preservative to be used in accordance with the invention.

The compositions may be applied onto or into the eyes. For example, the compositions may be used as a surgical irrigant.

In another embodiment of the invention, compositions useful for preserving ophthalmic compositions are provided. Such compositions include a magainin antimicrobial peptide, an analog of a magainin antimicrobial peptide or a mixture thereof present in an amount effective as a preservative. This effective amount may be less than about 10 milligrams per milliliter or less than about 1 milligram per milliliter or less than about 0.1 milligram per milliliter. In this embodiment, a sole preservative is used in the compositions. In a particularly useful embodiment of the invention, the compositions comprise magainin antimicrobial peptides. In another particularly useful embodiment of the invention, the compositions comprise an analog of a magainin antimicrobial peptide comprising the amino acid sequence GIGK-FLKKAKKFGKAFVKILKK (SEQ ID NO: 4). The compositions may also include water and an effective amount of a buffer to provide the compositions with a desired pH. Also, the compositions may include an effective amount of a tonicity component to provide the compositions with a desired osmolality.

The compositions exist in various forms. For example, the compositions may be an oil-in-water emulsion, a solution or a suspension.

The compositions may be applied onto or into the eyes. For example, the compositions may be used as a surgical irrigant.

In still another embodiment of the invention, compositions useful for preserving ophthalmic compositions are provided. Such compositions include a magainin antimicrobial peptide, an analog of a magainin antimicrobial peptide or a mixture thereof present in an amount effective as a preservative. This effective amount may be less than about 10 milligrams per milliliter or less than about 1 milligram per milliliter or less than about 0.1 milligram per milliliter. In this embodiment, the composition is an oil and water emulsion. In a particularly useful embodiment of the invention, the compositions comprise magainin antimicrobial peptides. In another particularly useful embodiment of the invention, the compositions comprise an analog of a magainin antimicrobial peptide comprising the amino acid sequence GIGKFLKKAKKFGKAFVKILKK (SEQ ID NO: 4). The compositions may also include water and an effective amount of a buffer to provide the compositions with a desired pH. Also, the compositions may include an effective amount of a tonicity component to provide the compositions with a desired osmolality.

The compositions may be applied onto or into the eyes. For example, the compositions may be used as a surgical irrigant.

In still another embodiment of the invention, compositions useful for preserving ophthalmic compositions are provided. Such compositions include an analog of a magainin antimicrobial peptide comprising the amino acid sequence GIGKFLKKAKKFGKAFVKILKK (SEQ ID NO: 4) present in an amount effective as a preservative. This effective amount may be less than about 10 milligrams per milliliter or less than about 1 milligram per milliliter or less than about 0.1 milligram per milliliter. The compositions may also include water and an effective amount of a buffer to provide the compositions with a desired pH. Also, the compositions may include an effective amount of a tonicity component to provide the compositions with a desired osmolality.

The compositions may exist as a solution or a suspension.

The compositions may be applied onto or into the eyes.

In still another embodiment of the invention, compositions useful for preserving ophthalmic compositions are provided. Such compositions include a magainin antimicrobial peptide, an analog of a magainin antimicrobial peptide or a mixture thereof present in an amount effective as a preservative. This effective amount may be less than about 10 milligrams per milliliter or less than about 1 milligram per milliliter or less than about 0.1 milligram per milliliter. These compositions are applied onto or into the eyes. In a particularly useful embodiment of the invention, the compositions comprise magainin antimicrobial peptides. The compositions also may include water and an effective amount of a buffer to provide the compositions with a desired pH. Also, the compositions may include an effective amount of a tonicity component to provide the compositions with a desired osmolality.

Also provided for are methods of preserving ophthalmic compositions. One such method comprises contacting an ophthalmic composition with a magainin antimicrobial peptide, analogs of magainin antimicrobial peptides or mixtures thereof present in an amount effective as a preservative in the composition. In one embodiment, the composition is an oil and water emulsion.

Also provided for are methods for treating an eye. One such method comprises contacting an eye with a liquid medium which includes magainin antimicrobial peptides, analogs of magainin antimicrobial peptides or mixtures thereof in an amount effective as a preservative. In one embodiment, the composition is an oil and water emulsion.

The invention also provides for ophthalmic compositions which comprise magainin antimicrobial peptides, analogs of magainin antimicrobial peptides or mixtures thereof in an amount effective as a preservative. In a particularly useful embodiment of the invention, the compositions comprise an analog of a magainin antimicrobial peptide comprising the amino acid sequence GIGKFLKKAKKFGKAFVKILKK (SEQ ID NO: 4). Also in a preferred embodiment, the composition is an oil-in-water emulsion and the composition is provided in a multidose format.

Any and all features described herein and combinations of such features are included within the scope of the invention provided that such features of any such combination are not mutually exclusive.

These and other aspects and advantages of the present invention are apparent in the following detailed description and claims.

DETAILED DESCRIPTION OF THE INVENTION

The present invention is applicable to preserving ophthalmic compositions, such as eye care compositions and contact lens care compositions which are benefited from being preserved.

One important feature of the compositions of the present invention is the inclusion of one or more antimicrobial peptides in the compositions.

In one embodiment, the present compositions include a sufficient amount of an antimicrobial peptide to effectively preserve the compositions. In a preferred embodiment, the antimicrobial peptide is a magainin antimicrobial peptide.

The antimicrobial peptides useful according to the present invention include naturally occurring antimicrobial peptides, preferably cytolytic peptides, synthetic antimicrobial peptides, antimicrobial peptide mimetics and nanotubes. Such peptides may be the L-form, the D-form or combinations or mixtures of both forms. At least some of these antimicrobial peptides may be membrane active. One or more of these antimicrobial peptides may act by disrupting a cell membrane.

Among the antimicrobial peptides preferably employed are those selected from defensins, peptides related to defensins, cecropins, peptides related to cecropins, and other amino acid polymers with antibacterial, antifungal and/or antiviral activities. Particularly preferred antimicrobial peptides employed in the present invention are magainin antimicrobial peptides and peptides related to magainin antimicrobial peptides and mixtures thereof.

Magainin antimicrobial peptides were first reported in the literature in 1987 (Zasloff (1987) Proc. Natl. Acad. Sci. USA 84, 5449–5453). Magainin antimicrobial peptides are a family of linear, amphipathic, cationic antimicrobial peptides, and are approximately 21 to 27 residues in length. It is believed that magainin antimicrobial peptides may exert their antimicrobial effect by disruption of cell membrane permeability.

Magainin antimicrobial peptides have numerous characteristics that make them a superior preservative for use in ophthalmic compositions. For example, magainin antimicrobial peptides are broad-spectrum antimicrobial agents which exhibit cidal activity against Gram-negative and Gram-positive bacteria, fungi and protozoa. Also, magainin antimicrobial peptides display a reduced eye irritation compared to existing preservatives for ophthalmic compositions. For example, benzalkonium chloride is known to exhibit ocular toxicity which may result in irritation or sensitivity to the eye. In addition, magainin antimicrobial peptides are highly water-soluble allowing effective antimicrobial action in an oil-in-water emulsion. This high water solubility also minimizes loss of effectiveness due to adsorption to plastic containers. Further, numerous magainin antimicrobial peptides and magainin antimicrobial peptide derivatives are available which increases the opportunities for avoiding incompatibilities with specific drugs or excipients in a particular formulation of a composition of the invention. Still further, magainin antimicrobial peptides have a low degree of bacterial resistance, are effective at very low concentrations and are easily produced by chemical synthesis or heterologous gene expression. Because of these and other factors magainin antimicrobial peptides are very well suited for use in the present invention.

Exemplary magainin antimicrobial peptides include the peptides having the following amino acid sequences:

```
Magainin I
Gly Ile Gly Lys Phe Leu His Ser Ala    (SEQ ID NO:
                                        1)
Gly Lys Phe Gly Lys Ala Phe Val Gly Glu Ile Met Lys Ser Magainin II
Gly Ile Gly Lys Phe Leu His Ser Ala    (SEQ ID NO:
                                        2)
Lys Lys Phe Gly Lys Ala Phe Val Gly Glu Ile Met Asn Ser
```

Exemplary magainin antimicrobial peptide analogs include the peptides having the following amino acid sequences:

```
MSI-78
Gly Ile Gly Lys Phe Leu Lys Lys Ala    (SEQ ID NO:
                                        3)
Lys Lys Phe Gly Lys Ala Phe Val Lys

Ile Leu Lys Lys-NH₂

MSI-344
Gly Ile Gly Lys Phe Leu Lys Lys Ala    (SEQ ID NO:
                                        4)
```

-continued
```
Lys Lys Phe Gly Lys Ala Phe Val Lys

Ile Leu Lys Lys
```

Other useful magainin antimicrobial peptide analogs and derivatives include magainin antimicrobial peptides having N-terminal positively charged chain extensions (e.g., (Lys)₁₀-magainin which enhances the antimicrobial activity of the peptides).

Additional magainin antimicrobial peptides, magainin antimicrobial peptide analogs and derivatives which are contemplated for use according to the present invention are described in U.S. Pat. Nos. 5,912,231, 5,847,047, 5,792,831, and 5,643,876 and in the publications Zasloff et al., Proc. Natl. Acad. Sci. USA 85, 910–913 (February 1988); Zasloff, Proc. Natl. Acad. Sci. USA 84, 5449–5453 (August 1987); and Bessale et al, Antimicrobial Agents, Chemotherapy 36 (No. 2), 313–317 (February 1992), and Maloy and Kari, Biopolymers 37, 105–122 (1995) each of which is incorporated in its entirety herein by reference.

Cecropins useful according to the invention include the peptides having the following amino acid sequences:

cecropin A:

```
Lys Trp Lys Leu Phe Lys Lys Ile Glu    (SEQ ID NO:
                                        5)
Lys Val Gly Gln Asn Ile Arg Asp Gly

Ile Ile Lys Ala Gly Pro Ala Val Ala

Val Val Gly Gln Ala Thr Gln Ile Ala

Lys;
``` and cecropin B:

```
Lys Trp Lys Val Phe Lys Lys Ile Glu    (SEQ ID NO:
                                        6)
Lys Met Gly Arg Asn Ile Arg Asn Gly

Ile Val Lys Ala Gly Pro Ala Ile Ala

Val Leu Gly Glu Ala Lys Ala Leu Gly
```

Cecropin D can also be employed.

Cecropin derivatives having C-terminus modifications, substitutions, and/or truncations which either enhance or do not inhibit antimicrobial activity are also contemplated for use according to the present invention. Useful derivatives include cecropin A amide (CA—NH₂), and cecropin A with a C-terminal ethylenediamine-modified homoserine (CA-Hse-NH-Et-NH₂). The general sequence homology of the N-terminus portion of the cecropins is necessary for activity and is therefore less suitable for truncation, modification, or substitution. However, analogs resulting from substitution of amino acids with similar chemical characteristics to the original can be designed. Maintaining an amphipathic helical structure similar to the original peptide will result in conservation of antimicrobial activity. An example of a substitution analog of cecropin B is Shiva-1:

```
Met Pro Arg Trp Arg Leu Phe Arg Arg    SEQ ID NO: 7)

Ile Asp Arg Val Gly Lys Gln Ile Lys

Gln Gly Ile Leu Arg Ala Gly Pro Ala

Ile Ala Leu Val Gly Asp Ala Arg Ala

Val Gly.
```

Shiva-1 and other cecropin substitution analogs having antimicrobial activity are contemplated as being useful according to the invention.

Defensins useful according to the invention include:

```
HNP-1 (human neutrophil peptide 1):
Ala Cys Tyr Cys Arg Ile Pro Ala Cys    SEQ ID NO: 8)

Ile Ala Gly Glu Arg Arg Tyr Gly Thr

Cys Ile Tyr Gln Gly Arg Leu Trp Ala

Phe Cys Cys;

HNP-2:
Cys Tyr Cys Arg Ile Pro Ala Cys Ile    (SEQ ID NO: 9)

Ala Gly Glu Arg Arg Tyr Gly Thr Cys

Ile Tyr Gln Gly Arg Leu Trp Ala Phe

Cys Cys;

HNP-3:
Asp Cys Tyr Cys Arg Ile Pro Ala Cys    (SEQ ID NO: 10)

Ile Ala Gly Glu Arg Arg Tyr Gly Thr

Cys Ile Tyr Gln Gly Arg Leu Trp Ala

Phe Cys Cys;

NP-1 (rabbit neutrophil peptide 1):
Val Val Cys Ala Cys Arg Arg Ala Leu    (SEQ ID NO: 11)

Cys Leu Pro Arg Glu Arg Arg Ala Gly

Phe Cys Arg Ile Arg Gly Arg Ile His

Pro Leu Cys Cys Arg Arg;
``` and the BNP-1 (bovine neutrophil peptide) sequence:

```
Arg Leu Cys Arg Val Val Ile Arg Val    (SEQ ID NO: 12)

Cys Arg.
```

Other defensins and defensin analogs, such as those described in Selsted et al, J. Clin. Invest. 76, 1436–1439 (October 1985), and Kagan et al, Proc. Natl. Acad. Sci. USA 87, 210–214 (January 1990), each of which is incorporated in its entirety herein by reference, are also useful in the present invention.

Tachyplesins, such as tachyplesin I and II, and polyphemusins, such as polyphemusin I and II, are defensin-like peptides. See, e.g., Ohta et al, Antimicrobial Agents and Chemotherapy 36 (No. 7), 1460–1465 (July 1992), which is incorporated in its entirety herein by reference. These peptides and antimicrobially active derivatives thereof are also contemplated as being useful in the present invention.

Other peptides, such as hybrids (peptides comprised of sequences from more than one antimicrobial class), e.g., cecropin-melittin hybrids, and peptide analogs in which one or more of the L-amino acids are replaced with other L-amino acids, can also be used with advantage provided that they retain sufficient antimicrobial activity.

Exemplary hybrid peptides include cecropin A-(1–8)-melittin-(1–18)-$NH_2$:

```
Lys Trp Lys Leu Phe Lys Lys Ile Gly    (SEQ ID NO:13)

Ile Gly Ala Val Leu Lys Val Leu Thr

Thr Gly Leu Pro Ala Leu Ile Ser-NH₂;
``` and cecropin A-(1–3)-melittin-(1–13)-$NH_2$:

```
Lys Trp Lys Gly Ile Gly Ala Val Leu    (SEQ ID NO:14)

Lys Val Leu Thr Thr Gly Leu-NH₂.
```

Melittin itself, however, is unsuitable for use due to its high toxicity.

Antimicrobial peptide mimetics are also contemplated for use with the present invention. Antimicrobial peptide mimetics may have a lower molecular weight than an average size antimicrobial peptide. These peptides may comprise components such as modified thiazole and/or oxazole moieties. Antimicrobial peptide mimetics may be membrane active molecules that function by disrupting cell membranes. At least one type of antimicrobial peptide mimetic can be obtained from Genaera Corp., Plymouth Meeting, Pa.

The antimicrobial agents must be compatible with the composition being preserved. The antimicrobial peptides should also be non-toxic to humans.

Antimicrobial agents useful according to the present invention can be prepared using techniques well known to those skilled in the art. For example, antimicrobial peptides can be prepared by solid-phase synthesis or using heterologous gene expression. Exemplary processes for preparing antimicrobial peptides are given in Wade et al, Proc. Natl. Acad. Sci. USA 87, 4761–4765 (June 1990), Bessale et al, FEBS Letters 274, No. 1,2, 151–155 (November 1990), and Biochem. Biophys. Res. Commun. 277(3) 675–580 (November 2000) each of which is incorporated herein by reference in its entirety.

A second antimicrobial component can be employed in the present invention that is other than the first antimicrobial component. This second antimicrobial component can be selected from substantially non-oxidative antimicrobial components and mixtures thereof.

As used herein, substantially non-oxidative antimicrobial components include effectively non-oxidative organic chemicals, for example, synthetic polymers, which derive their antimicrobial activity through a chemical or physiochemical interaction with the microbes or microorganisms. Suitable non-oxidative antimicrobial components include, but are not limited to, quaternary ammonium salts used in ophthalmic applications such as poly[dimethylimino-2-butene-1,4-diyl]chloride, alpha-[4-tris(2-hydroxyethyl) ammonium]-dichloride (chemical registry number 75345-27-6, available under the trademark polyquarternium 1® from ONYX Corporation), benzalkonium halides, and biguanides such as salts of alexidine, alexidine-free base, salts of chlorhexidine, hexamethylene biguanides and their polymers, antimicrobial polypeptides, and the like and mixtures thereof. A particularly useful substantially non-oxidative antimicrobial component is selected from polyhexamethylene biguanide (PHMB), N-alkyl-2-pyrrolidone, chlorhexidine, polyquaternium-1, hexetidine, bronopol, alexidine, ophthalmically acceptable salts thereof and mixtures thereof.

The salts of alexidine and chlorhexidine can be either organic or inorganic and are typically gluconates, nitrates, acetates, phosphates, sulphates, halides and the like. Generally, the hexamethylene biguanide polymers, also referred to as polyaminopropyl biguanide (PAPB), have molecular weights of up to about 100,000. Such compounds are known and are disclosed in Ogunbiyi et al U.S. Pat. No. 4,758,595, the disclosure of which is incorporated in its entirety herein by reference.

The substantially non-oxidative antimicrobial components useful in the present invention are preferably present in the liquid aqueous medium in concentrations in the range of about 0.000005% or about 0.00001% to about 2% (w/v).

More preferably the substantially non-oxidative antimicrobial component is present in the liquid aqueous medium at an ophthalmically acceptable or safe concentration.

The concentration of preservative selected depends, for example, on the effectiveness of the specific preservative in preventing growth, or the killing, of bacteria, fungi, and/or protozoa in a preserved composition. Concentration of preservative selected may also depend on the effectiveness of the specific preservative in reducing the microbial load on a contact lens.

The present compositions may conveniently be presented as solutions or suspensions in aqueous liquids or non-aqueous liquids, or as oil-in-water or water-in-oil liquid emulsions. The present compositions may include one or more additional ingredients which are conventionally employed in compositions of the same general type.

The present compositions in the form of aqueous suspensions may include excipients suitable for the manufacture of aqueous suspensions. Such excipients are suspending agents, for example, sodium carboxymethylcellulose, methylcellulose, hydroxypropyl-methylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadeca-ethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof.

The present compositions in the form of oily suspensions may be formulated in a vegetable oil, for example, olive oil, castor oil, soy oil, sesame oil or coconut oil, or in a mineral oil such as liquid paraffin. Such suspensions may contain a thickening agent, for example beeswax, hard paraffin or cetyl alcohol.

The present compositions may also be in the form of oil-in-water emulsions. The oily phase may be a vegetable oil, for example, castor oil, olive oil, soy oil, or arachis oil, or a mineral oil, for example, liquid paraffin, and the like and mixtures thereof. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate.

Also included within the scope of this invention are preserved compounds which increase in viscosity upon administration to the eye. For example, "gelling polysaccharides" which are disclosed in U.S. Pat. No. 5,212,162 which is incorporated in its entirety herein by reference. Also disclosed in this patent are ophthalmic formulations containing carrageenans and furcellarans which are administered as partially gelled liquids which gel upon instillation into the eye. Additionally, U.S. Pat. Nos. 4,136,173, 4,136,177, and 4,136,178, disclose the use of therapeutic compositions containing xanthan gum and locust bean gum which are delivered in liquid form to the eye and which gel upon instillation. U.S. Pat. No. 4,861,760 discloses ophthalmological compositions containing gellan gum which are administered to the eye as non-gelled liquids and which gel upon instillation. Each of these four patents is incorporated in its entirety herein by reference.

Also within the scope of this invention are preserved oils, ointments, gels and the like.

One or more additional components can be included in the present compositions based on the particular application for which the compositions are formulated. For example, the present compositions can be formulated to include a therapeutic component to be administered to the eyes. In one embodiment, the therapeutic component is an antibiotic. In a preferred embodiment, the antibiotic is cyclosporin A. In another embodiment, the therapeutic component is a steroid. In a preferred embodiment, the steroid is proednislone acetate. These are merely examples of therapeutic components that may be included in the compositions of the invention. Any therapeutic component that may advantageously be included in the present compositions is within the scope of this invention.

The present compositions may include components, such as cyclodextrins, to enhance the solubility of one or more other components included in the compositions. Cyclodextrins are widely known in the literature to increase the solubility of poorly water-soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: β-cyclodextrin, derivatives of β-cyclodextrin, β-cyclodextrin, derivatives of β-cyclodextrin, β-cyclodextrin, derivatives of β-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. As used herein, the term "derivatives" as it relates to a cyclodextrin means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

The specific cyclodextrin component selected should have properties acceptable for the desired application. The cyclodextrin component should have or exhibit reduced toxicity, particularly if the composition is to be exposed to sensitive body tissue, for example, eye tissue, etc. Very useful cyclodextrin components include beta-cyclodextrin, derivatives of β-cyclodextrin and mixtures thereof. Particularly useful cyclodextrin components include sulfobutylether β-cyclodextrin, hydroxypropyl β-cyclodextrin and mixtures thereof. Sulfobutylether β-cyclodextrin is especially useful, for example, because of its substantially reduced toxicity.

The amount of cyclodextrin component in the present compositions should be effective to perform the desired function or functions in the present composition and/or perform the desired function or functions after administration to a human or animal. The amount of cyclodextrin component preferably is sufficient to complex at least in a major amount, and more preferably substantially all, of the active component in the present composition. In one useful embodiment, the amount of cyclodextrin component in the present composition is in the range of about 0.1% to about 30% (w/v) or more of the composition.

An additional component or additional components included in the present compositions may be selected from components which are conventionally used in one or more contact lens care compositions. For example, the present compositions may be formulated as preserving compositions, disinfecting compositions, cleaning compositions, wetting compositions, conditioning compositions, soaking compositions and the like. Examples of such additional components include buffering agents, cleaning agents, wetting agents, sequestering agents, viscosity builders, tonicity agents, nutrient agents, contact lens conditioning agents, antioxidants, pH adjustors, and the like. These additional components are each included in the present compositions in an amount effective to impart or provide the beneficial or desired property to the compositions. For example, such additional components may be included in the present compositions in amounts similar to the amounts of such components used in other ophthalmic compositions.

Also, the present compositions may be formulated to be useful in performing two or more contact lens care operations. For example, for contact lens care, a preserved disinfecting/cleaning composition, or a preserved cleaning/conditioning composition or even an all-purpose lens care composition may be formulated and such multi-functional compositions are included within the scope of the present invention.

A surfactant component may be included in the present compositions. The surfactant component preferably is non-ionic. Exemplary surfactant components include, but are not limited to, nonionic surfactants, for example, polysorbates (such as polysorbate 80-Trademark Tween® 80), 4-(1,1,3,3-tetramethylbutyl) phenol/poly(oxyethylene) polymers (such as the polymer sold under the trademark Tyloxapol®), poly(oxyethylene)-poly(oxypropylene) block copolymers, glycolic esters of fatty acids and the like, and mixtures thereof. The surfactant may be selected from poly(oxyethylene)-poly(oxypropylene) block copolymers and mixtures thereof. Such surfactant components may be obtained commercially from the BASF Corporation under the trademark Pluronic®. Such block copolymers may be generally described as polyoxyethylene/polyoxypropylene condensation polymers terminated in primary hydroxyl groups.

The amount of surfactant component, if any, present varies over a wide range depending on a number of factors, for example, the specific surfactant or surfactants being used, the other components in the composition and the like. Often the amount of surfactant is in the range of about 0.005% or about 0.01% to about 0.1% or about 0.5% or about 1.0% or about 2.5% (w/v).

Useful buffering agents include, but not limited to, acetate buffers, citrate buffers, phosphate buffers and borate buffers. Acids and bases may be used to adjust the pH of the present compositions as needed.

Useful wetting agents include, but are not limited to, polyvinyl alcohol, polyoxamers, polyvinyl pyrrolidone, hydroxypropyl methyl cellulose and mixtures thereof.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxypropyl methylcellulose, carboxymethyl cellulose, polyvinyl pyrrolidone, polyvinyl alcohol and mixtures thereof.

Useful antioxidants include, but are not limited to, sodium metabisulfite, sodium thiosulfate, N-acetylcysteine, butylated hydroxyanisole, butylated hydroxytoluene and mixtures thereof.

The present preserved compositions may be administered to the eyes. These compositions, formulated appropriately, may be used in place of prior conventional compositions. For example, the compositions may be use in administering a therapeutic component to the eyes. In one embodiment, an antibiotic is administered to the eyes in a composition of the invention. In another example, the compositions of the invention may be used as a surgical irrigant. These and other compositions of the present invention may be packaged in a multiple dose format container.

The present compositions may also be used in the care of a contact lens, for example, to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result.

The following examples are set out to illustrate, but not limit, the scope of this invention.

EXAMPLE 1

The following composition is prepared by blending together the ingredients.

| Ingredient | % w/v |
| --- | --- |
| Magainin | 0.0001 |
| Castor Oil | 1.25 |
| Glycerine | 2.2 |
| Polysorbate 80 | 1.0 |
| Cyclosporin A | 0.1 |
| Carbomer (stabilizer) | 0.05 |
| Purified Water | Q.S. to 100% |

This composition is formulated as and is effective as a composition for the treatment of dry eye.

EXAMPLE 2

Thirty-four patients report symptoms of moderate to severe dry eye (grittiness, dryness, sensation that something is in the eye, tearing, burning). The patients are treated (eye drop) twice daily from a multidose container of the composition of Example 1. The treatment period is 12 weeks. After 8–12 weeks of treatment, improvements are seen in the dry eye symptoms of all the patients. All patients report improvements in the sandy, gritty feeling as well as improvements in dryness and itching. Improvements in the signs of dry eye are also noted when the patients are examined by an ophthalmologist (rose bengal staining of the cornea and superficial punctate keratitis).

There are no apparent adverse effects from the use of the magainin antimicrobial peptide containing composition of Example 1. For example, there is no bacterial overgrowth, and no increased risk of ocular infection demonstrated. The treatments are well tolerated by the patients with no noted irritation or increased sensitivity.

EXAMPLE 3

The following composition is prepared by blending together the ingredients.

| Ingredient | % w/v |
| --- | --- |
| Magainin | 0.0001 |
| Hydroxyethyl cellulose | 0.65 |
| Sodium chloride | 0.67 |
| Boric acid | 0.39 |
| Sodium borate decahydrate | 0.20 |
| Edetate disodium | 0.127 |
| Purified Water | Q.S. to 100% |

This composition is formulated as and is effective as a preserved soft contact lens cleaning composition.

EXAMPLE 4

The following composition is prepared by blending together the ingredients.

| Ingredient | % w/v |
| --- | --- |
| MSI-344 | 0.0001 |
| Hydroxyethyl cellulose | 0.65 |
| Sodium chloride | 0.67 |
| Boric acid | 0.39 |
| Sodium borate decahydrate | 0.20 |
| Edetate disodium | 0.127 |
| Purified Water | Q.S. to 100% |

This composition is formulated as and is effective as a preserved soft contact lens soaking/conditioning composition.

EXAMPLE 5

The following composition is prepared by blending together the ingredients.

| Ingredient | % w/v |
| --- | --- |
| Hydroxypropyl beta-cyclodextrin | 22.0 |
| Prednisolone acetate | 1.0 |
| Hydroxypropylmethyl cellulose | 0.25 |
| Antimicrobial peptide mimetic | 0.01 |
| Sodium acetate | 0.08 |
| Hydrochloric acid | adjust to pH 4.5 |
| Purified Water | Q.S. to 100% |

This composition is formulated for and is effective for treatment of inflammatory disorders of the ocular tissue.

What is claimed is:

1. An ophthalmic composition comprising a carrier component, and a preservative component selected from the group consisting of magainin antimicrobial peptides, analogs of magainin antimicrobial peptides and mixtures thereof present in an amount effective as a preservative in said composition, wherein said composition is an oil-containing emulsion or an oil-containing suspension.

2. The composition of claim 1 wherein said preservative component is present in an effective amount less than about 10 milligrams per milliliter.

3. The composition of claim 1 which further comprises an effective amount of a buffer component to provide said composition with a desired pH.

4. The composition of claim 1 which further comprises an effective amount of a tonicity component to provide said composition with a desired osmolality.

5. The composition of claim 1 wherein said preservative component is a magainin antimicrobial peptide.

6. The composition of claim 1 wherein said preservative component is an analog of a magainin antimicrobial peptide comprising the amino acid sequence of SEQ ID NO: 4.

7. An ophthalmic composition comprising a carrier component, said composition further comprising an antimicrobial peptide mimetic present in an amount effective as a preservative in said composition, wherein said composition is an oil-containing emulsion or an oil-containing suspension.

8. The composition of claim 7 wherein said antimicrobial peptide mimetic is present in an effective amount less than about 10 milligrams per milliliter.

9. The composition of claim 7 which further comprises water and an effective amount of a buffer component to provide said composition with a desired pH.

10. The composition of claim 7 which further comprises an effective amount of a tonicity component to provide said composition with a desired osmolality.

11. The composition of claim 7 wherein said composition further includes a therapeutically effective component.

12. A method of preserving an ophthalmic composition comprising:

contacting an ophthalmic composition with a magainin analog with an amino acid sequence comprising of SEQ ID NO: 4 in an amount effective as a preservative in said composition, wherein said composition is an oil-containing emulsion or an oil-containing suspension.

13. An ophthalmic composition comprising a magainin antimicrobial analog with an amino acid sequence comprising of SEQ ID NO: 4 present in an amount effective as a preservative in said composition, wherein said composition is provided in a multidose format and wherein said composition is an oil-containing emulsion or an oil-containing suspension.

14. The composition of claim 1, further comprising an effective amount of a therapeutically effective component.

15. The composition of claim 14, wherein the therapeutically effective component comprises an antibiotic.

16. The composition of claim 15, wherein the antibiotic is cyclosporin.

17. The composition of claim 14, wherein the therapeutically effective component comprises a steroid.

18. The composition of claim 17, wherein the steroid is prednisolone acetate.

19. The composition of claim 1, wherein the preservative component is the sole preservative in said composition.

20. The composition of claim 1, wherein the composition is a surgical irrigant.

21. The composition of claim 1, further comprising a second antimicrobial component.

22. The composition of claim 21, wherein the second antimicrobial component is a substantially non-oxidative antimicrobial component.

* * * * *